(12) United States Patent
Ye et al.

(10) Patent No.: US 9,282,982 B2
(45) Date of Patent: Mar. 15, 2016

(54) SURGICAL MILLING CUTTER BRACKET

(75) Inventors: Lei Ye, Chongqing (CN); Jian Zhou, Chongqing (CN); Hua Feng, Chongqing (CN); Fei Li, Chongqing (CN); Hengyang Zhu, Chongqing (CN); Congxiao Li, Chongqing (CN)

(73) Assignee: CHONGQING RUNZE PHARMACEUTICAL CO., LTD., Chongqing (CN)

( * ) Notice: Subject to any disclaimer, the term of this patent is extended or adjusted under 35 U.S.C. 154(b) by 268 days.

(21) Appl. No.: 13/823,021

(22) PCT Filed: Aug. 24, 2011

(86) PCT No.: PCT/CN2011/078850
§ 371 (c)(1),
(2), (4) Date: Mar. 13, 2013

(87) PCT Pub. No.: WO2012/041137
PCT Pub. Date: Apr. 5, 2012

(65) Prior Publication Data
US 2013/0178861 A1    Jul. 11, 2013

(30) Foreign Application Priority Data
Sep. 30, 2010   (CN) .......................... 2010 1 0298081

(51) Int. Cl.
*A61B 17/32*         (2006.01)
*A61B 17/17*         (2006.01)
*A61B 17/16*         (2006.01)
(52) U.S. Cl.
CPC .............. *A61B 17/17* (2013.01); *A61B 17/1633* (2013.01); *A61B 17/32002* (2013.01); *A61B 17/1613* (2013.01)

(58) Field of Classification Search
CPC ................................................. A61B 17/32002
USPC ............. 606/96, 167–170, 79, 80–85; 279/75
See application file for complete search history.

(56) References Cited

U.S. PATENT DOCUMENTS

| | | | | |
|---|---|---|---|---|
| 3,308,828 A | * | 3/1967 | Pippin ................ | A61B 17/1695 606/168 |
| 3,682,177 A | * | 8/1972 | Ames .................. | A61B 17/1695 403/13 |
| 3,867,932 A | * | 2/1975 | Huene .................... | A61B 17/17 606/104 |
| 5,505,737 A | * | 4/1996 | Gosselin et al. ................ | 606/79 |
| 5,733,289 A | * | 3/1998 | Seedhom ........... | A61B 17/1677 606/80 |
| 5,755,718 A | * | 5/1998 | Sklar .................. | A61B 17/1604 606/170 |

(Continued)

FOREIGN PATENT DOCUMENTS

CN            201211208 Y   *   3/2009

*Primary Examiner* — David Bates

(57) ABSTRACT

A surgical milling cutter bracket includes a retaining base having a through hole. The upper part of the retaining base is provided with a finger guide having an L-shaped support frame on the top of the finger guide. A downward protrusion is provided at the end of the short side of the L-shaped support frame. The lowest point of the protrusion is lower than the lowest point of the cylindrical head of the milling cutter during normal operation of the milling cutter. A bolt having a through hole at the center is fixed within the cavity of the finger guide. A depressor is provided on the upper part of the retaining base. The bolt passes through a hole of the depressor and is connected to a nut. The protrusion is able to prevent an object from contacting the cylindrical head, thus avoiding cutting the object unevenly.

4 Claims, 1 Drawing Sheet

(56) References Cited

U.S. PATENT DOCUMENTS

| | | | | |
|---|---|---|---|---|
| 5,769,853 A * | 6/1998 | Quetin | ................ | A61F 2/4644 433/229 |
| 7,115,119 B2 * | 10/2006 | Desarzens | .......... | A61B 17/1666 606/1 |
| 8,900,260 B2 * | 12/2014 | Ye | ........................ | A61B 17/162 279/75 |

* cited by examiner

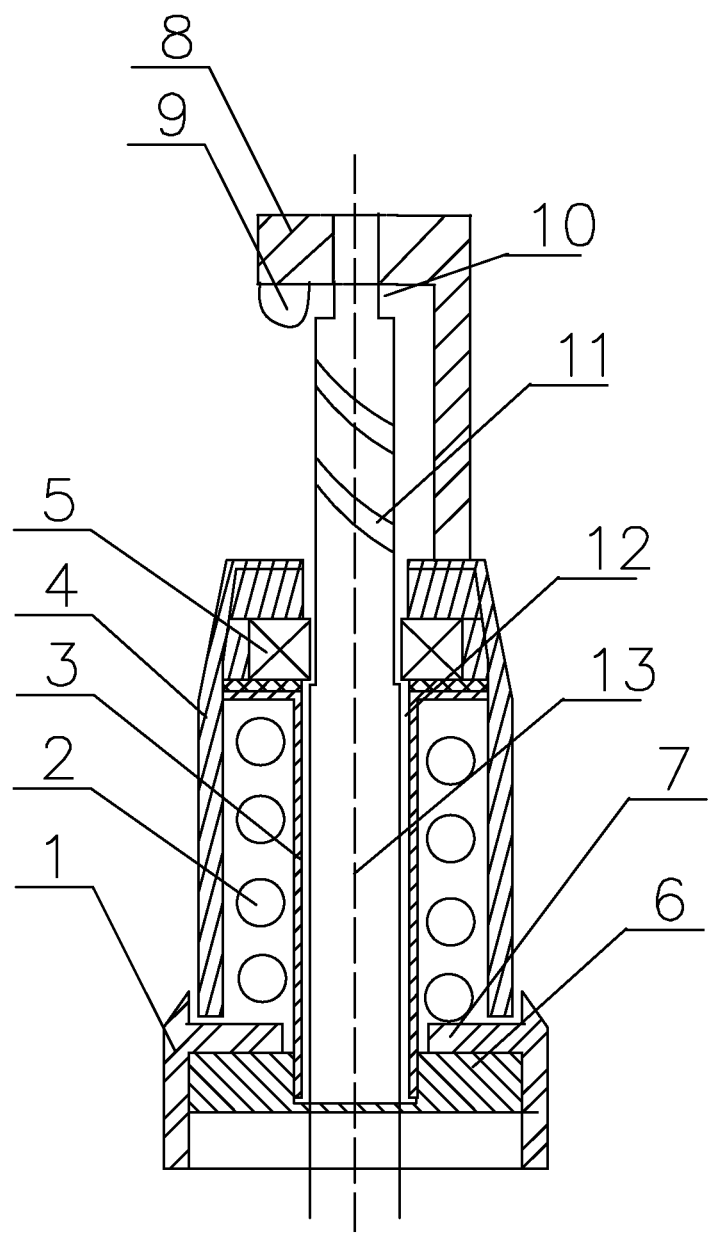

SURGICAL MILLING CUTTER BRACKET

BACKGROUND OF THE INVENTION

1. Field of the Invention

The present invention relates to a surgical cutting machine, and more particularly to a surgical milling cutter bracket.

2. Description of the Prior Art

During a surgical operation, a milling cutter is used for cutting. The milling cutter of a prior art comprises a milling cutter bracket, a blade and an electric motor. A top of the milling cutter bracket has an L-shaped support frame. A short side of the L-shaped support frame has a hole. The cylindrical head at the front part of the blade of the milling cutter extends into the hole to ensure that the milling cutter provides a better support to secure the blade, especially in rotation. In order to protect the milling cutter, the cylindrical head doesn't fully extend into the hole so a portion of the cylindrical head is exposed. In the existing technology, the short side of the L-shaped support frame is a flat configuration. With the cylindrical head of the prior art placed above the blade, when cutting an object, the cylindrical head doesn't function as it was designed to cut an object if it touches and levels with the object, as the blade itself then does not contact the object. The object will be cut unevenly. During cutting, it is difficult for the milling cutter of the prior art to change direction when rotating along a vertical axis of the cutter.

Accordingly, the inventor of the present invention has devoted himself based on his many years of practical experiences to solve these problems.

SUMMARY OF THE INVENTION

The primary object of the present invention is to provide a surgical milling cutter bracket which can prevent a cylindrical head from contacting an object to be cut. The surgical milling cutter bracket is nimble to change direction.

In order to achieve the aforesaid object, a surgical milling cutter bracket comprises a retaining base having a through hole. The upper part of the retaining base is provided with a finger guide having an L-shaped support frame on the top of the finger guide to be manually controlled by a user's finger(s) to guide the direction of the cutter's rotation. A downward protrusion is provided at a distal end of a short side of the L-shaped support frame. The lowest point of the protrusion is lower than the lowest point of a cylindrical head of the milling cutter during normal operation of the milling cutter.

A bolt having a through hole is fixed within a cavity of the finger guide. A depressor is provided on the upper part of the retaining base. The bolt passes through a hole of the depressor and is connected to a nut.

Alternatively, the lower part of the retaining base is provided with a finger guide. A T-shaped bolt having a through hole is fixed within a cavity of the finger guide. A depressor is provided on the upper part of the retaining base. A nut passes through a hole of the depressor and is connected to the bolt.

For keeping stable working of the milling cutter, the upper part of the finger guide is provided with a bearing.

To prevent the finger guide from being too nimble, a spring is fitted on the bolt.

For skidproof, the outer surfaces of the retaining base and the finger guide each have a skidproof groove.

The protrusion of the present invention is able to prevent an object from contacting the cylindrical head, thus avoiding cutting the object unevenly. Additionally, by driving the L-shaped support frame to rotate via the finger guide, the movement direction of the milling cutter can be changed, facilitating the operation.

BRIEF DESCRIPTION OF THE DRAWINGS

FIG. 1 is a sectional view according to a preferred embodiment of the present invention.

DETAILED DESCRIPTION OF THE PREFERRED EMBODIMENTS

Embodiments of the present invention will now be described, by way of example only, with reference to the accompanying drawings.

As shown in FIG. 1, a surgical milling cutter bracket comprises a retaining base (1) having a through hole (12). A vertical central axis (13) of the through hole (12) is shown by the dashline. A milling cutter (11) is inserted into the through hole (12). The upper part of the retaining base (1) is attached with a finger guide (4) having an L-shaped support frame on the top of the finger guide (4).

A downward protrusion (9) is provided at a distal end of a short side (8) of the L-shaped support frame. The lowest point of the protrusion (9) is lower than the lowest point of a cylindrical head (10) of the milling cutter (11) during normal operation of the milling cutter (11). This arrangement can prevent an object from contacting the cylindrical head (10), thus avoiding cutting the object unevenly. A T-shaped bolt (3) having a through hole (12) is fixed within the cavity of the finger guide (4). A depressor (7) is provided on the upper part of the retaining base (1). A nut (6) passes through a hole of the depressor (7) and is connected to the bolt (3).

The upper part of the finger guide (4) is provided with a bearing (5). A spring (2) is fitted on the bolt (3). The outer surfaces of the retaining base (1) and the finger guide (4) each have a skidproof groove. The bearing (5) makes the milling cutter (11) have a closer force point to ensure working of the milling cutter (11). The spring (2) is to ensure a certain force between the finger guide (4) and the retaining base (1), preventing the finger guide (4) from turning too much to cause an operating error.

When the finger guide (4) is turned along the vertical central axis (13), the bolt (3) and the nut (6) are driven to turn.

Thus, by driving the L-shaped support frame to rotate via the finger guide, the movement direction of the milling cutter (11) can be changed, facilitating the operation.

Although particular embodiments of the present invention have been described in detail for purposes of illustration, various modifications and enhancements may be made without departing from the spirit and scope of the present invention.

Accordingly, the present invention is not to be limited except as by the appended claims.

What is claimed is:

1. A surgical milling cutter bracket, comprising
a retaining base (1) having a through hole (12), into which a milling cutter (11) is inserted,
an upper part of the retaining base (1) being attached with a finger guide (4) having an L-shaped support frame on a top of the finger guide (4) rotatable by the finger guide (4),
a downward protrusion (9) extending downwards perpendicular to a short side (8) being fixing to a distal end of the short side (8) of the L-shaped support frame, wherein the short side (8) runs perpendicular to a vertical central axis (13) of the through hole (12), around which the finger guide (4) rotates, a lowest point of the protrusion (9) being lower than a lowest point of a cylindrical head (10) of the milling cutter (11) during operation of the milling cutter (11);

a bolt (3) having a through hole (12) being fixed within a cavity inside of the finger guide (4), rotatable by the finger guide (4), a depressor (7) extending and fixed to the upper part of the retaining base (1) over a nut (6) beneath to attach the finger guide (4) to the retaining base (1), and the bolt (3) passing through a hole of the depressor (7) and being connected to the nut (6), such that the milling cuter (11) can be driven to rotate by the finger guide (4).

2. The surgical milling cutter bracket as claimed in claim 1, wherein an upper part of the finger guide (4) is provided with a bearing (5) to abut against the milling cutter (11) for securing the milling cutter (11) in position within the cavity.

3. The surgical milling cutter bracket as claimed in claim 1 or 2, wherein a spring (2) is fitted on the bolt (3), contributing a force between the finger guide (4) and the retaining base (1) to prevent the finger guide (4) from turning too much during operation.

4. The surgical milling cutter bracket as claimed in claim 3, wherein outer surfaces of the retaining base (1) and the finger guide (4) each have a skidproof groove as an obstacle to possible slippage of a user's finger(s) during operation.

* * * * *